United States Patent [19]

Brasca et al.

[11] Patent Number: 4,973,674

[45] Date of Patent: Nov. 27, 1990

[54] CHIRAL SYNTHESIS OF ANTHRACYCLINES FROM SUBSTITUTED ANTHRAQUINONES

[75] Inventors: Maria G. Brasca; Sergio Penco, both of Milan, Italy

[73] Assignee: Farmitalia Carlo Erba S.R.L., Milan, Italy

[21] Appl. No.: 179,989

[22] Filed: Apr. 11, 1988

[30] Foreign Application Priority Data

Apr. 14, 1987 [GB] United Kingdom ................. 8708927

[51] Int. Cl.$^5$ ........................................ C07H 15/244
[52] U.S. Cl. ..................................... 536/6.4; 536/55.3
[58] Field of Search ................. 536/6.4, 55.3; 514/34, 514/908; 552/262

[56] References Cited

U.S. PATENT DOCUMENTS

| | | | |
|---|---|---|---|
| 4,021,457 | 5/1977 | Kende et al. | 552/262 |
| 4,067,969 | 1/1978 | Penco et al. | 514/34 |
| 4,070,382 | 1/1978 | Kende et al. | 552/262 |
| 4,125,607 | 11/1978 | Arcamone et al. | 514/34 |
| 4,147,706 | 4/1979 | Kende et al. | 552/262 |
| 4,161,480 | 7/1979 | Pappo et al. | 552/262 |
| 4,322,412 | 3/1982 | Cassinelli et al. | 514/34 |
| 4,325,947 | 4/1982 | Penco et al. | 514/34 |
| 4,348,388 | 9/1982 | Garland et al. | 536/6.4 |
| 4,353,894 | 10/1982 | Acton et al. | 514/34 |
| 4,415,498 | 11/1983 | Anathasubramanian et al. | 552/220 |
| 4,477,444 | 10/1984 | Suarato et al. | 536/6.4 |
| 4,536,336 | 8/1985 | Kishi | 552/262 |
| 4,537,882 | 8/1985 | Horton et al. | 514/34 |
| 4,697,005 | 9/1987 | Swenton et al. | 536/6.4 |
| 4,839,346 | 6/1989 | Bargiotti et al. | 514/34 |

FOREIGN PATENT DOCUMENTS

| | | |
|---|---|---|
| 0024727 | 3/1981 | European Pat. Off. . |
| 0051280 | 5/1982 | European Pat. Off. . |
| 2804099 | 8/1978 | German Democratic Rep. . |
| 54-141759 | 11/1979 | Japan . |
| 61-78797 | 4/1986 | Japan . |
| 0298674 | 10/1928 | United Kingdom . |
| 2033393 | 5/1980 | United Kingdom . |
| 2067552 | 7/1981 | United Kingdom . |
| 2116169 | 9/1983 | United Kingdom . |

OTHER PUBLICATIONS

Jackson et al.; J.C.S. Chem. Comm. (1981), pp. 478–479.
Acton et al.; J. Med. Chem. 17(6): 659–660 (1974).
Lee et al.; J. Org. Chem. 41 (13): 2296–2303, (1976).
Smith et al.; J. Org. Chem. 42(23):3653–3660 (1977).
Russell et al.; Tetrahedron Letters 25(14): 1517–1520 (1984).
Tetrahedron, (1984), vol. 40, pp. 4657–4667, "Recent Aspects of Anthracyclinone Chemistry, 'An Efficient Enanthiocontrolled Synthesis . . . '", R. Gupta et al.

Primary Examiner—Ronald W. Griffin
Assistant Examiner—Nancy S. Carson
Attorney, Agent, or Firm—Oblon, Spivak, McClelland, Maier & Neustadt

[57] ABSTRACT

Anthracycline glycosides of formula (I):

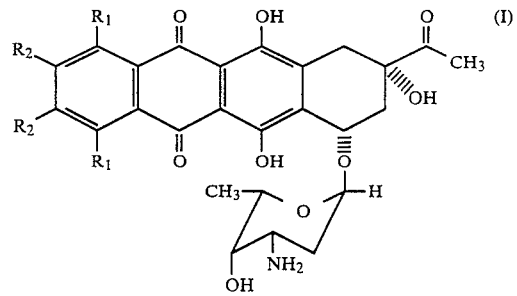

wherein $R_1$ and $R_2$ are independently selected from hydrogen, methyl, ethyl or methoxy and pharmaceutically acceptable acid addition salts thereof, which are useful in treatment of human cancer, are prepared by a stereospecific condensation of a derivative of daunosamine of general formula (II):

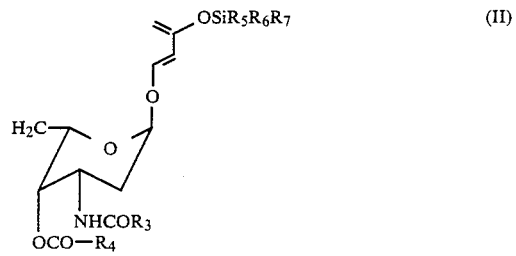

wherein $R_3$ is an alkyl, perfluoroalkyl or aryl group and $R_4$, $R_5$, $R_6$ and $R_7$ are independently selected from alkyl, aryl or aralkyl having up to ten carbon atoms, with a quinone quinizarine epoxide of general formula (III)

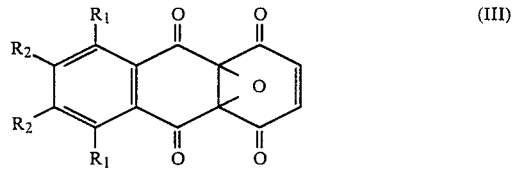

and conversion of the product obtained to the anthracycline glycoside of formula (I) or salt thereof.

2 Claims, No Drawings

CHIRAL SYNTHESIS OF ANTHRACYCLINES FROM SUBSTITUTED ANTHRAQUINONES

DESCRIPTION

This invention relates to a multistep method for the stereospecific synthesis of anthracyclines of general formula (I):

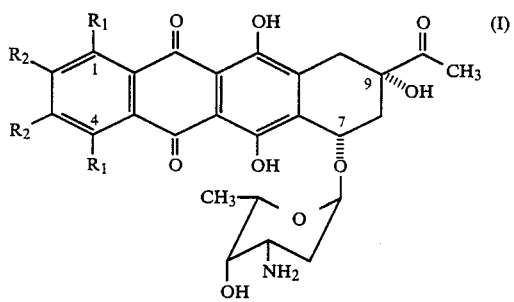

wherein $R_1$ and $R_2$ are independently selected from hydrogen, methyl, ethyl and methoxy, and pharmaceutically acceptable acid addition salts thereof.

Anthracyclines of general formula (I) exhibit a strong antitumor activity. 4-Demethoxydaunomycin for example (I, $R_1=R_2=H$;) has a higher anti-leukemic activity than daunomycin and adriamycin and is also effective by oral administration. Many synthetic approaches to the aglycones anthracyclinones have been disclosed. However, the methods are generally inadequate to prepare them in optically pure form. The invention provides a sequence of sterospecific reactions leading to the desired anthracyclines (I) in the optically pure form as required for therapeutic use.

Accordingly, the present invention provides a stereospecific process for the preparation of an anthracycline glycoside of general formula (I):

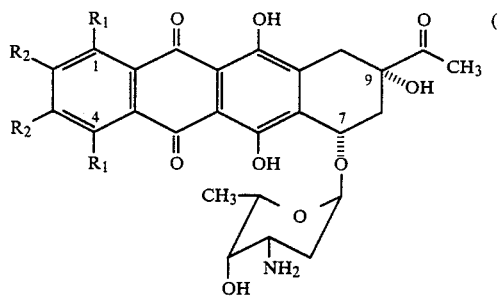

wherein $R_1$ and $R_2$ are independently selected from hydrogen, methyl, ethyl or methoxy, or a pharmaceutically acceptable acid addition salt thereof; which process comprises (i) reacting a daunosamine silyl derivative of general formula (II):

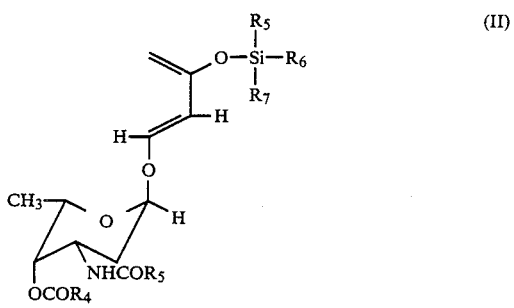

wherein $R_3$ is an alkyl, perfluoroalkyl or aryl group and $R_4$, $R_5$, $R_6$ and $R_7$ are independently selected from alkyl, aryl or aralkyl having up to ten carbon atoms, with a quinone quinizarine epoxide of general formula (III):

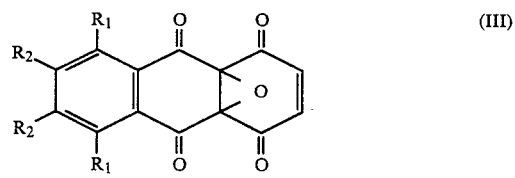

in an inert organic solvent;

(ii) removing the silyl group from the protected tetracyclic derivative of general formula (VIII):

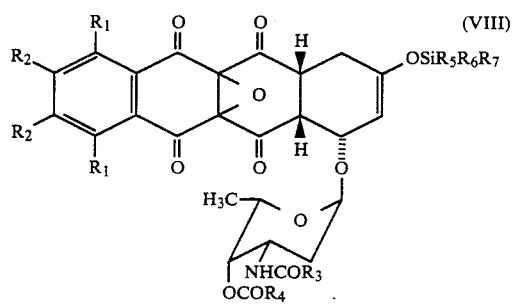

wherein $R_1$, $R_2$, $R_3$, $R_4$, $R_5$, $R_6$ and $R_7$ are as above defined, in an inert organic solvent;

(iii) converting the resultant ketone of general formula (IX):

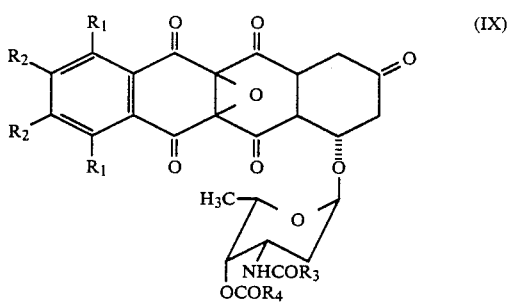

wherein $R_1$, $R_2$, $R_3$ and $R_4$ are as defined above, into the intermediate compound of general formula (X):

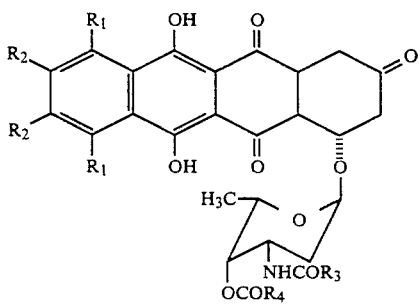

wherein $R_1$, $R_2$, $R_3$ and $R_4$ are as defined above; and (iv) converting the compound of general formula (X) into an anthracycline glycoside of formula (I) or a pharmaceutically acceptable acid addition salt thereof.

The compounds of formula (II) also form part of the invention. Preferably $R_3$ represents a $C_1$–$C_4$ alkyl, perfluoromethyl or phenyl group. Preferably, $R_4$, $R_5$, $R_6$ and $R_7$ are each independently a $C_1$–$C_4$ alkyl, phenyl or benzyl group. More preferably, $R_4$ is p-nitro-phenyl and $R_5$, $R_6$ and $R_7$ each represent methyl.

A compound of formula (II) is prepared according to the invention by a process which comprises (A) converting a daunosamine of formula (IV):

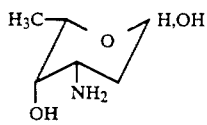

or an acid addition salt thereof, into a protected derivative of general formula (V):

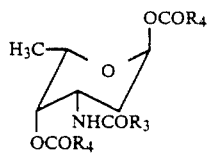

wherein $R_3$ and $R_4$ are as defined in above;

(B) selectively deacylating the protected derivative of general formula (V) to give a daunosamine N,O protected derivative of general formula (VI):

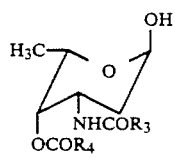

wherein $R_3$ and $R_4$ are as defined above;

(C) reacting the daunosamine N,O protected derivative of formula (VI) with 3-butyn-2-one to give a mixture of the α- and β-anomeric compounds of general formula (VII) and (VIIA):

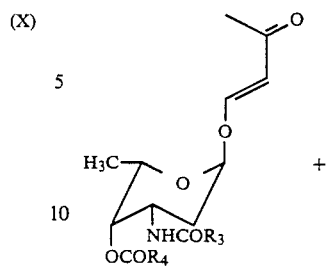

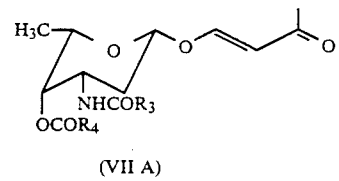

(VII A)

wherein $R_3$ and $R_4$ are as defined above;

(D) separating the α-anomeric compound of formula (VII) from the β-anomeric compound of formula (VIIA); and (E) silylating the α-anomeric compound of formula (VII) so as to obtain the compound of formula (II).

The general reaction scheme is set forth in the SCHEME below. It includes the key steps of synthesising the hitherto, unknown daunosamine derivatives (II) and of condensing this compound with a quinone quinizarine epoxide (III). The latter can be easily prepared from commercially available starting material according to known methods (e.g. U.S. Pat. Nos. 4,021,457, 4,070,382, J. Org. Chem. 41, 2296 (1976) and J. Chem. Soc. Chem. Comm. 1981, 478 and the references quoted therein).

The daunosamine derivative (II) is prepared from a naturally occurring aminosugar daunosamine (IV) or an acid addition salt thereof, preferably the hydrochloride. For this purpose, compound (IV) is initially transformed into the intermediate (V) according well known methods [e.g. T. H. Smith et al., J. Org. Chem. 42, 3653 (1977)]. The intermediate (V) is then selectively deacylated (deacetylated when $R_4$ is methyl) to give the daunosamine N,O protected derivative (VI). Such selective deacylation is performed typically by dissolving the compound (V) in an organic solvent such as one chosen from ketones, esters, aliphatic or cycloaliphatic ethers and polyethers. The compound (V) may then be treated with a catalytic amount of a mineral acid, for example by adding at least one equivalent of $H_2O$ and a catalytic amount of mineral acid. 4N aqueous hydrochloric acid may be used. The reaction time generally from 2 to 24 hours and the temperature should be kept at from $-10°$ C. to $+50°$ C.

The next step of the present invention consists in reacting (VI) with 3-butyn-2-one. Typically, at least one equivalent of the 3-butyn-2-one is used. Preferably, the reaction is effected in the presence of a catalytic amount of an aliphatic or cycloaliphatic amine, generally a tertiary amine such as trimethylamine, triethylamine, tripropylamine, N-alkylpyrrolidine, N-alkylpiperidine, N-alkylpiperidine, N-alkylmorpholine and tetramethylguanidine. The reaction is normally carried out in an inert organic solvent, preferably an aromatic hydrocarbon such as benzene, toluene or xylene. The reaction may take place at about 80° C. for about 1 hour. A mixture of the product (VII) and of its anomer (VIIA) is formed. The desired compound (VII) can be isolated from the mixture by conventional methods such as fractional crystallisation or chromatography. The latter is generally preferred giving (VII) in very pure form. The anomer (VIIA) which can not be used for the purpose of the present invention can be transformed back to the starting material (VI) and can therefore be used for further preparations of (VII).

The compound (VII) is silylated such as to obtain the silyl derivative (II). For the purpose, (VII) is preferably dissolved in an anhydrous inert organic solvent, preferably chosen among aromatic hydrocarbons or chlorinated aromatic or aliphatic hydrocarbons (e.g. $CH_2Cl_2$, $CHCl_3$, $C_2H_4Cl_2$, chlorobenzene, benzene or toluene) or their mixtures. Normally an inert atmosphere is employed. Compound (VII) can be reacted with a silyl derivative of general formula $$SiR_5R_6R_7Y$$

where $R_5$, $R_6$, $R_7$ are independently selected in the group of alkyl or aryl-alkyl having up to ten carbon atoms and Y represents Cl, Br, I, CN, $NHSiR_5R_6R_7$, $$\underset{|}{\overset{CH_3}{N}}=C-OSiR_5R_6R_7,$$

$CF_3SO_2$ or $S-SiR_5R_6R_7$. Typically at least one equivalent of the silyl derivative $SiR_5R_6R_7Y$ is used and reaction is carried out in the presence of at least one equivalent (based on the compound (II)) of a tertiary aliphatic amine is added. Trimethyl- or triethyl-amine are preferred. The reaction generally lasts for at least 1 h at a temperature between $-20°$ C. and $50°$ C.

A Diels Alder condensation is then effected between the compound (II) and the quinizarine epoxide (III). The reaction conditions for the Diels Alder condensation may vary in accordance with the substitution pattern in the aromatic ring of the quinone quinizarine epoxide and according to the nature of $R_4$, $R_5$, $R_6$, $R_7$ on the diene compound (II). Generally, however, the reaction is carried out in an inert organic solvent such an aromatic hydrocarbon or aliphatic or aromatic chlorohydrocarbon at a temperature of from $-10°$ C. to $+60°$ C. The reaction is best run at room temperature for from 10 to 24 hours.

Evaporation of the most part of the solvent and addition of diethyl-ether can give a precipitate consisting in pure (VIII) which has not only the desired tetracyclic skeleton but above all it has the daunosamyl group at the $C_7$ in the desired absolute configuration. The removal of the silyl group from the compound (VIII) can be performed according to conventional methods e.g. hydrolytic cleavage typically in the presence of strong acids. For this purpose, (VIII) may be dissolved in an inert solvent selected from ethers, esters, ketones, hydrocarbons and chloro-carbons and shaken with 0.01 to 2 equivalents of a mineral or organic acid, eventually dissolved in water.

Transformation of (IX) into (X) can be obtained in a single step by action of a molar excess of trimethyl silyl iodide. This may be prepared "in situ", from sodium or potassium iodide and trimethyl silyl iodide. This reaction is normally run in an anhydrous solvent. Acetonitrile gives the best result and is the solvent of choice if trimethyl silyl iodide has to be prepared "in situ". Other anhydrous solvents can be used without detriment, however. Normally, the reaction is effected under a nitrogen atmosphere. Conventional work up such as dilution with a solvent immiscible with water, washing with water and with aqueous solution of $Na_2S_2O_3$ (to remove the formed elemental iodine), drying and removal of the solvent gives (X).

The compound (X) is then converted into an anthracycline glycoside (I) or pharmaceutically acceptable salt thereof. Known methods can be used. They are here exemplified to stress the practical relevance of the present invention in the synthesis of anthracyclines but they must be considered in no way a limitation of the present invention. Thus, a glycoside (I) or salt thereof may be prepared by (a) converting the compound of general formula (X) into a 9-ethynyl derivative of general formula (XI):

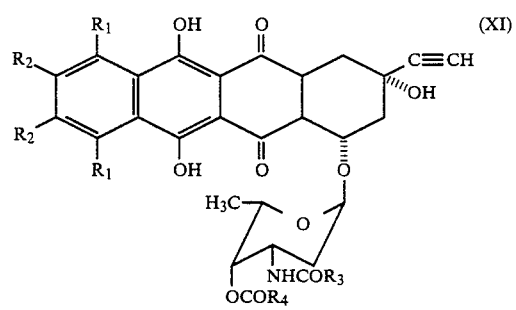

wherein $R_1$, $R_2$, $R_3$ and $R_4$ are as defined above;

(b) oxidising the 9-ethynyl derivative of formula (XI) to obtain a compound of general formula (XII):

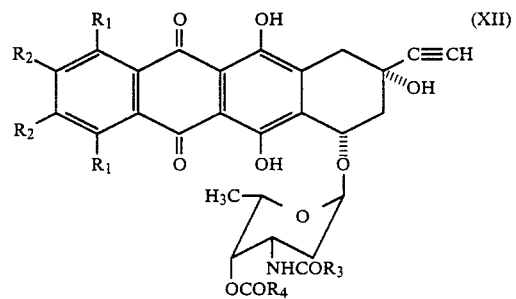

wherein $R_1$, $R_2$, $R_3$ and $R_4$ are as defined above;

(C) hydrating the compound of formula (XII) to give an N,O protected daunorubicin derivative of general formula (XIII):

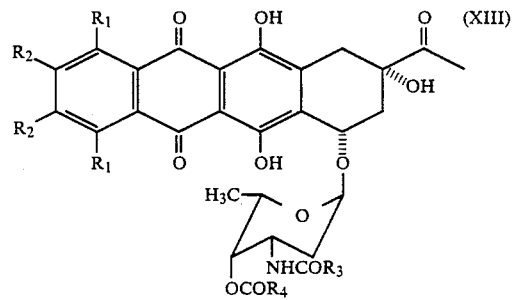

wherein $R_1$, $R_2$, $R_3$ and $R_4$ are as defined above;

(d) removing the N- and O-protecting groups from the compound of formula (XIII) to obtain an anthracycline glycoside of general formula (I); and (e) if desired, converting the anthracycline glycoside of formula (I) into a pharmaceutically acceptable acid addition salt thereof.

The compound (X) for example can react with an ethynyl metal derivative of general formula M—C≡CH (where M=Li, Na, BrMg, ClMg, ½ Mg) to give a derivative (XI). This reaction may be effected at 0° C. in dry tetrahydrofuran using 30 equivalents of the ethynyl metal derivative. The resultant compound (XI) can be oxidized e.g. with lead tetraacetate to give the compound (XII). Reaction may take place for 24 hours. The compound (XII) can subsequently be hydrated using HgO and aqueous $H_2SO_4$ to give the N,O protected daunorubicin derivative (XIII). The compound (XII), dissolved in acetone, may be treated with red mercuric oxide and 7% aqueous $H_2SO_4$ under reflux for 5 minutes.

Removal by hydrolysis of the $R_4CO$ and $R_3CO$ groups leads to the glycoside (I). This can be effected by conventional hydrolytic procedures such as mild alkaline hydrolysis. Thus, the N,O protected daunorubicin derivative (XIII) may be treated with 0.1N aqueous NaOH at room temperature for one hour. Preferably, the resultant anthracycline glycoside (I) is converted into the hydrochloride salt thereof. This may be achieved by treating the glycoside (I) with methanolic 0.1N hydrogen chloride and the resultant hydrochloride salt is isolated.

The invention also provides pharmaceutical compositions comprising an anthracycline glycoside of formula (I), or a pharmaceutically acceptable acid addition salt thereof, prepared according to the present invention and a pharmaceutically acceptable carrier or diluent. Such compositions contain a therapeutically effective amount of the glycoside or its salt. Conventional formulations, carriers and diluents may be employed.

The following Examples illustrate the invention.

EXAMPLE 1

Preparation of:
2,3,6-trideoxy-4-O-p-nitrobenzoyl-3-N-trifluoroacetamido-α-L-lyxohexopyranose (VI)

To a solution of 2,3,6-trideoxy-1,4-di-O-p-nitrobenzoyl-3-N-trifluoroacetamido-α-L-lyxohexopyranose (V) (2 g 3.69 mmol.) in acetone (20 ml) were added 3 ml of 4N HCl. After 12 h the reaction mixture was concentrated in vacuo, dissolved in ethyl acetate (20 ml) and washed with saturated water solution of sodium bicarbonate and subsequently with water, dried over $Na_2SO_4$ and evaporated to afford 1.35 g of (VI) (93% of yield on V)

| | |
|---|---|
| $H^2$—NMR [300MHz,(CD$_3$)$_2$SO] | 1.05 (d, 3H, —CH$_3$) |
| | 4.3 (q, 1H, 5 —H) |
| | 5.3 (d, 1H, 4 —H) |
| | 5.4 (d, 1H, 1 —H) |
| | 6.6 (brs, 1H, OH) |
| EI-MS m/e 391 | |

EXAMPLE 2

Preparation of
(E)-4-(2',3',6'-trideoxy-4'-O-p-nitrobenzoyl-3'-N-trifluoroacetamido-α-L-lyxohexopyranosyl)oxy-but-3-en-2-one (VII)

To a suspension of (VI) (10 g 25 mmol in toluene (300 ml) at 80° C. were added 3-butyn-2-one (2.4 ml 30 mmol and triethylamine (350μp 2.5 mmol.

The reaction was stirred at 80° C. for 3h, allowed to cool to room temperature.

Diethyl ether was then added (co. 300 ml).

The formed precipitated was collected, washed with diethyl ether to afford 10.8 g (94% of yield) of a mixture of α,β anomers.

Crystallization of this material from chloroform gave pure β-anomer (VIIA) (5.3 g).

The mother liquor was purificated by flashcromatography to give pure α-anomer (VII) (5.4 g) that was crystallized from diethyl ether.

| | |
|---|---|
| α-anomer (VII) | |
| m.p. 140–142° C. | |
| IR KBr | 1730 (C = O) |
| | 1685 (C = O insaturated) |
| UV (ETOH) | 237 nm |
| $H^1$—NMR 300 MHZ, (CD$_3$)$_2$SO | (d, 3H, CH$_3$) |
| | 1.95 (1H, dd, 2'-Hax) |
| | 2.15 (3H, s, CH$_3$C = O) |
| | 2.45 (1H, dt, 2'-Heq) |
| | 4.2 (1H, q, 5'-H) |
| | 4.45 (1H, m, 3'-H) |
| | 5.35 (1H, d, 4'-H) |
| | 5.75 (1H, d, 1'-H = 1.8 Hz) |
| | 5.8 (1H, d, 3-H = 12.5 Hz) |
| | 7.75 (1H, d, 4-H = 12.5 Hz) |
| | 8.22 (2H, d, Arom.) |
| | 8.42 (2H, d, Arom.) |
| | 9.65 (1H. d. NH) |
| MS-DCI: m/e 460 | |
| β-anomer (VII A) | |
| m.p. 100° C. | |
| $H^1$—NMR 300 MHz, (CD$_3$)$_2$SO inter alia 5.25 (1H, d, 4'-H) | |
| 5.35 (1H, dd, 1-H 5.8 and 6.2 Hz) | |

EXAMPLE 3

Preparation of (E)-1-[2',3',6'-trideoxy-4'-O-p-nitro benzoyl-3'-N-trifluoracetamido-α-L-lyxohexopyranosyl)oxy]-3-trimethylsilyloxybuta-1,3diene (II $R_5$=$R_6$=$R_7$=CH$_3$)

To a stirred mixture of fused Zinc chloride (200 mg 1.47 mmol) and triethylamine (5.5 ml 40 mmol) a solution of (VII) (2.3 g 5 mmol) in methylene chloride (30 ml) was added, followed by trimethylsilylchloride (2.5 ml 20 mmol).

The mixture was stirred at room temperature overnight, then diethyl ether was added and the mixture was filtered.

After usual work-up a white solid was obtained (2.1 g 78% of yield on VII)

| | |
|---|---|
| $H^1$—NMR (300 MHz, CDCl$_3$) | 0.26 (s, 9H, CH$_3$—Si) |
| | 1.1 (d, 3H, —CH$_3$) |
| | 4.2 (q, 1H, 5'-H) |
| | 4.2 (d, 2H, 4-H$_2$) |
| | 5.45 (d, 1H, 1'-H) |
| | 5.35 (d, 1H, 4'H) |
| | 5.7 (d, 1H, 2-H) |
| | 6.8 (d, 1H, 1-H) |

-continued

MS-DCl: m/e 532

EXAMPLE 4

Preparation of (VIII) by reaction of epoxytetrone (III) with the diene (II)

A solution of (III) (1.016 g 4 mmol) and (II) (2.13 g 4 mmol) in dry toluene (80 ml) was stirred at room temperature for 24 h.

After evaporation of solvent, the addition of diethyl ether gave (VIII) as a colourless precipitate (2.3 g 74% of yield)

| m.p. 153–155° C. | |
|---|---|
| $H^1$—NMR (300 MHz, CDCl$_3$) | 0.3 (s, 9H, CH$_3$—Si) |
| | 1.1 (d, 3H, CH$_3$) |
| | 3.9 (t, 1H, 10a-H) |
| | 3.2 (dd, 1H, 10a-H) |
| | 4.1 (q, 1H, 5'-H) |
| | 4.55 (dd, 1H, 7-H) |
| | 5.0 (d, 1H, 4'H) |
| | 5.1 (d, 1H, 8-H) |
| | 5.2 (d, 1H, 1'-H) |
| MS-DCI m/e 786 | |

EXAMPLE 5

Preparation of (IX)

A solution of (VIII) (1.0 g 1.27 mmol) in freshly distilled THF (15 ml) was treated with 0.1N HCl (1 ml).

When the hydrolysis was completed (TLC analysis) (6 h), the mixture was diluted with methylene chloride (50 ml), washed with water and dried over Na$_2$SO$_4$. Evaporation of the organic layer gave (IX) as colourless solid (0.7 g. 77% of yield).

| $H^1$—NMR (300 MHz, CDCl$_3$) | 1.1 (d, 3H, CH$_3$) |
|---|---|
| | 3.5 (dd, 1H, 6a-H) |
| | 4.8 (q, 1H, 7-H) |
| | 5.05 (d, 1H, 4'-H) |
| | 5.2 (d, 1H, 4'-H) |
| MS-DCI: m/e 714 | |

EXAMPLE 6

Preparation of compound (X)

To a solution of sodium iodide (3.9 mmol 0.585 g) in anhydrous acetonitrile (5 ml) trimethylsilylchloride (1.9 mmol 240μl) was added dropwise under nitrogen. After few minutes, a solution of (IX) (0.93 g 1.3 mmol) in anhydrous acetonitrile (3 ml) was slowly added.

After 30' the mixture reaction was tracted with 5N aq sodium thiosulphate (20 ml), extracted with ethylacetate (three portions of 20 ml), and washed with water, dried over Na$_2$SO$_4$ and evaporated to give (X)(0,7 g 77% of yield) as pale yellow solid.

| $H^1$—NMR (300 MHz, CDCl$_3$) | 1.2 (d, 3H, CH$_3$) |
|---|---|
| | 3.55 (dd, 1H, 6a-H) |
| | 3.82 (dt, 1H, 10a-H) |
| | 4.05 (q, 1H, 5'-H) |
| | 4.68 (q, 1H, 7-H) |
| | 4.84 (d, 1H, 1'-H) |
| | 5.3 (d, 1H, 4'-H) |
| | 12.8 and 13.7 (s, each 1H, 5 and 12-OH) |

EXAMPLE 7

Preparation of 4-demethoxy daunomycin hydrochloride (I-HCl)

To a solution of (X)(0.8 g 1.14 mmol) in dry THF (80 ml) at 0° C. a solution of CH≡CMgBr in THF, (30 ml of 1N solution corresponding to ca 30 mol equiv) was added.

After 1 h the mixture was poured into an ice-cold saturated solution of NH$_4$Cl and extracted with methylene chloride. The organic layer was washed with water, dried over Na$_2$SO$_4$ and evaporated to leave (XI) which was dissolved in acetic acid (15 ml) and lead tetraacetate (500 mg 1.12 mmol) was added. After 24 h water was added to the mixture to give (XII) as a red precipitate that was filtered and dried.

This precipitate was dissolved in acetone (75 ml) and treated with red HgO (0.6 g, 2.76 mmol) and 7% aqueous H$_2$SO$_4$ (75 ml).

The mixture was heated under reflux for 5' and allowed to cool to room temperature. After usual work-up a red solid was obtained (XIII) (0.425 g 50% of yield based upon (X).

0.3 g of (XIII) (R$_3$=CF$_3$; R$_4$=—C$_6$H$_4$NO$_2$) (0.4 mmol) was dissolved in 100 ml of 0.1N NaOH and kept at room temperature for 1 h. The solution was brought to pH 8 with 5N HCl and extracted with methylene chloride.

Evaporation of the solvent left a residue that was taken up in 3 ml of a mixture of chloroform-methanol 3:2 (v:v). Methanolic 0.1N HCl was added to adjust the pH to 4.5, after which sufficient diethyl ether was added to precipitate 0.13 g of the hydrochloride of 4-demethoxy-daunomycin

| (I—HCl) |
|---|
| mp 183–185° C. |
| $[\alpha]_D^{20}$ = +205° (c = 0.1 MeOH) |

SCHEME

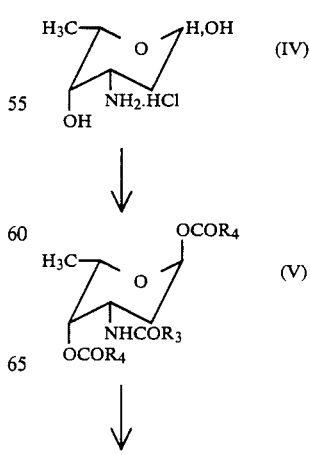

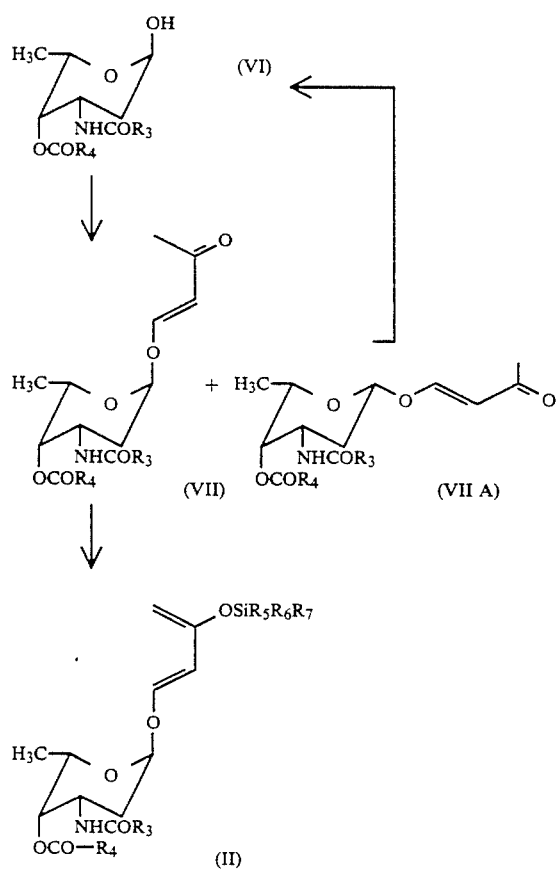
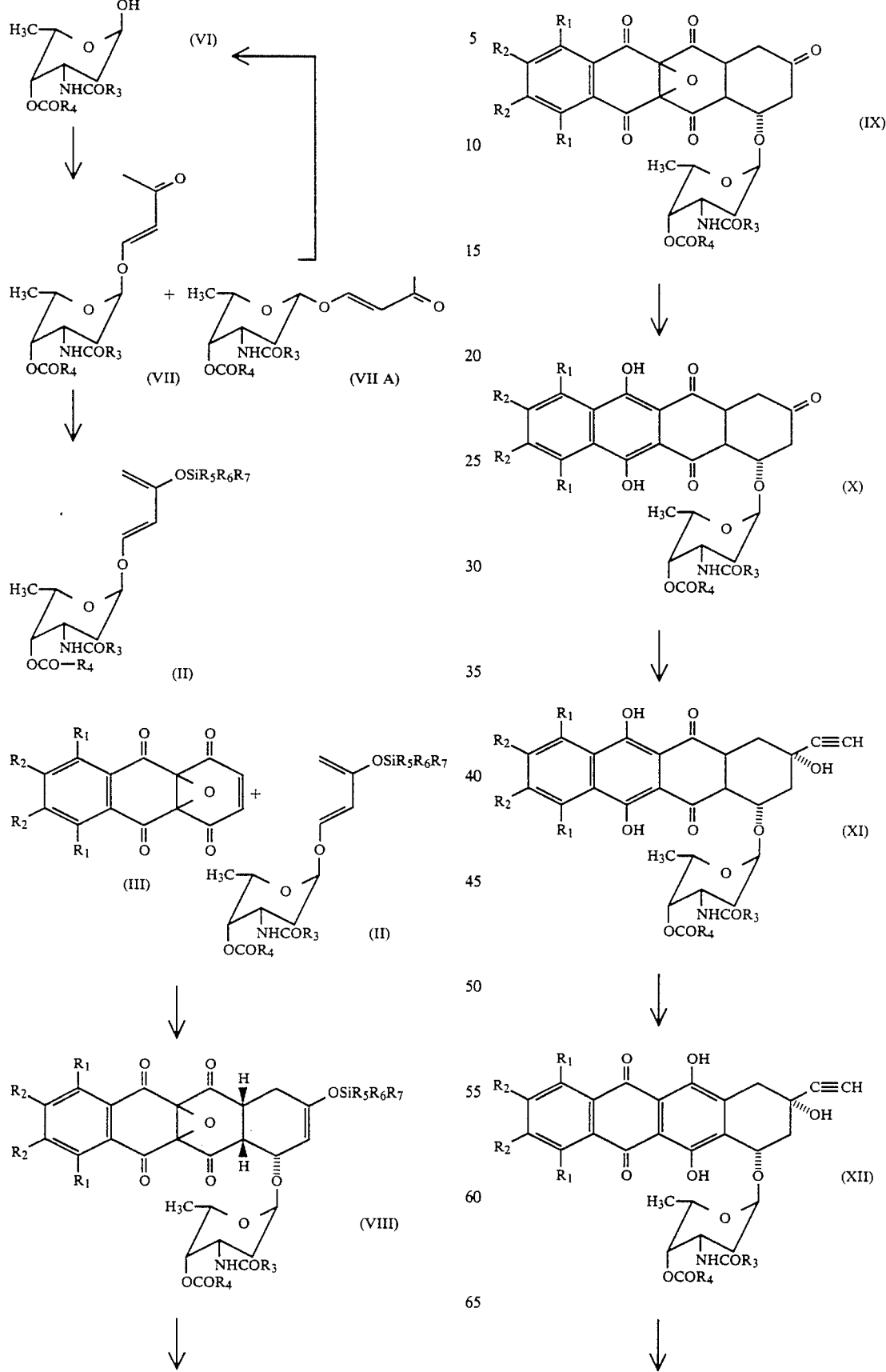

-continued

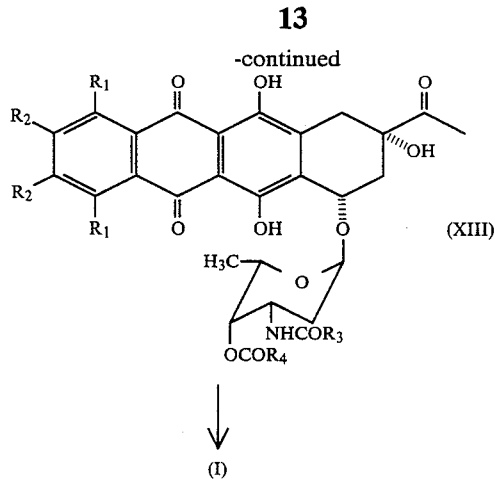

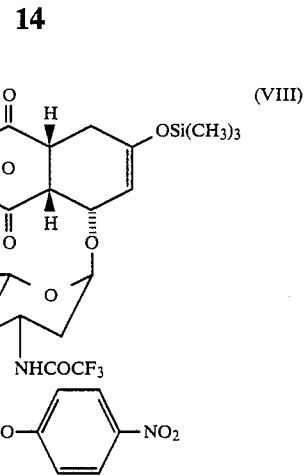

We claim:
1. A stereospecific process for the preparation of 4-demethoxydaunorubicin of formula (I), comprising the steps of:

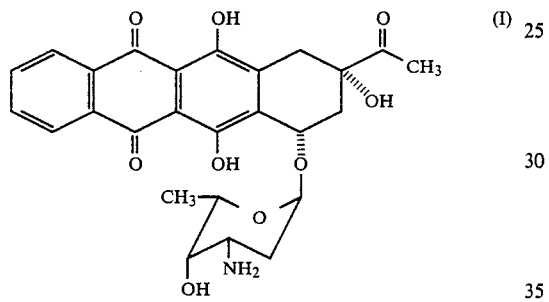

dissolving the quinone quinizarine epoxide of formula (III):

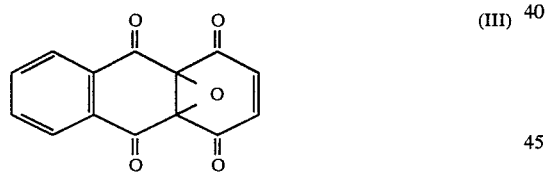

in dry toluene,
reacting said epoxide at room temperature and for 24 hours, with a daunosamine of formula II:

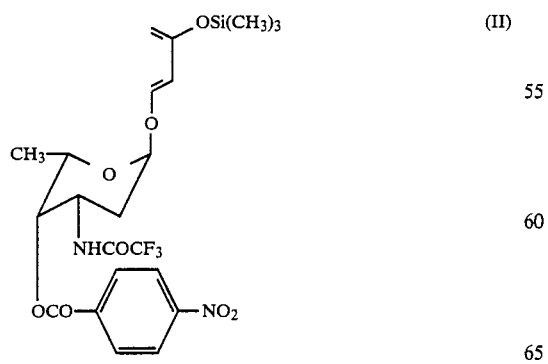

to give a protected tetracyclic compound of formula (VIII):

having the 7(S) configuration, hydrolytically clearing the group in tetrahydrofuran with 0.1N hydrochloric acid to give a ketone of formula (IX):

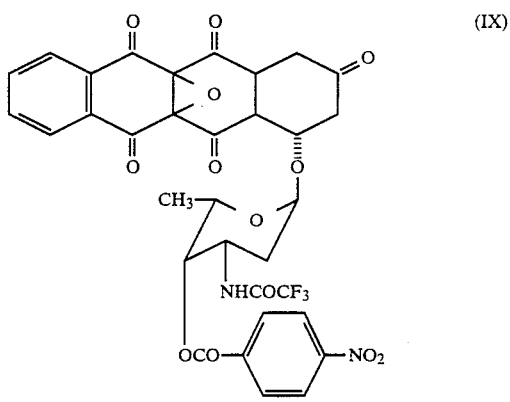

dissolving said ketone in anhydrous acetonitrile and treating said dissolved ketone with sodium iodide and trimethylsilyl chloride under a nitrogen atmosphere, to obtain the compound of formula (X):

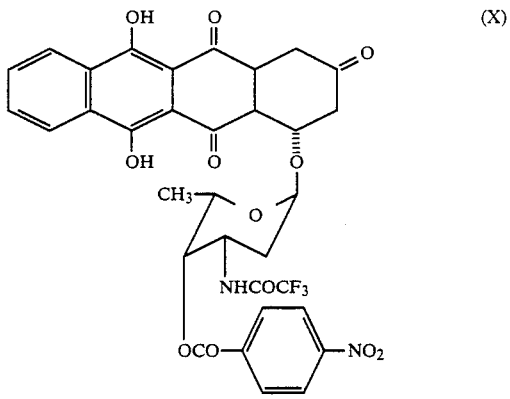

treating said compound (X) at a temperature of 0° C., in anhydrous tetrahydrofuran with an excess of ethynyl magnesium bromide to give the compound of formula (XI):

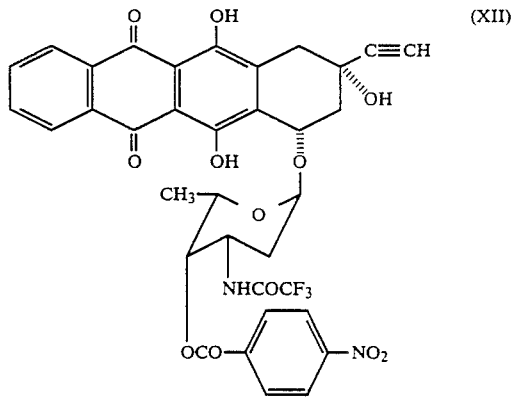

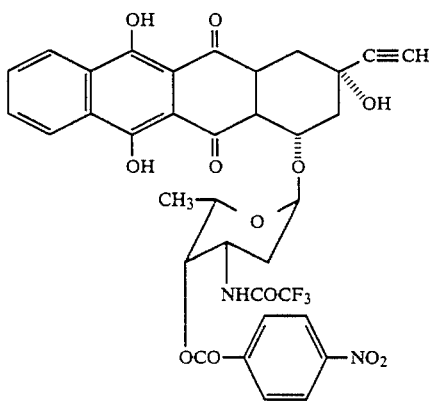

treating said compound of formula (XI) with lead tetracetate in acetic acid to obtain the compound of formula (XII):

reacting said compound of formula (XII) with red mercuric oxide and aqueous 7% sulphuric acid to give the N,O-protected 4-demethoxydaunorubicin of formula (XIII):

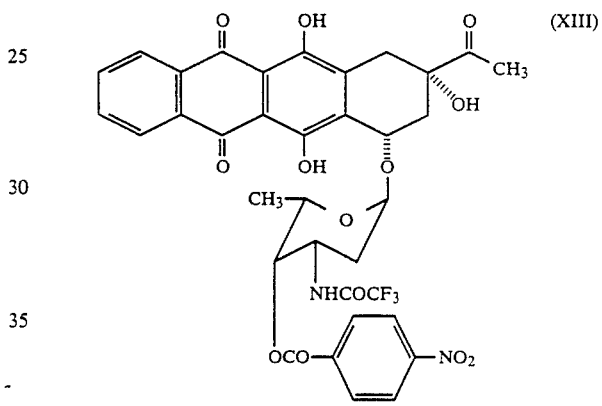

hydrolysing said compound of formula (XIII) in 0.1N aqueous sodium hydroxide, at room temperature, to give the 4-demethoxydaunorubicin of formula (I).

2. The process of claim 1, further comprising treating the 4-demethoxydaunorubicin of formula (I) with anhydrous hydrochloric acid in methanol to form the hydrochloride salt of the 4-demethoxydaunorubicin of formula (I).

* * * * *

UNITED STATES PATENT AND TRADEMARK OFFICE
CERTIFICATE OF CORRECTION

PATENT NO. : 4,973,674
DATED : NOVEMBER 27, 1990
INVENTOR(S) : MARIA G. BRASCA ET AL.

It is certified that error appears in the above-identified patent and that said Letters Patent is hereby corrected as shown below:

ON TITLE PAGE:     Item [21]
   In the Appl. No., please delete "179,989" and insert

--179,999--.

Signed and Sealed this

Seventh Day of July, 1992

Attest:

DOUGLAS B. COMER

Attesting Officer          Acting Commissioner of Patents and Trademarks